US00PP29857P3

(12) United States Plant Patent
Jernigan

(10) Patent No.: US PP29,857 P3
(45) Date of Patent: Nov. 20, 2018

(54) ***GARDENIA* PLANT NAMED '4KIMYMJ01'**

(50) Latin Name: *Gardenia jasminoides*
Varietal Denomination: 4KIMYMJ01

(71) Applicant: Brian J. Jernigan, Dearing, GA (US)

(72) Inventor: Brian J. Jernigan, Dearing, GA (US)

(73) Assignee: Center for Applied Nursery Research, Inc., Dearing, GA (US)

( * ) Notice: Subject to any disclaimer, the term of this patent is extended or adjusted under 35 U.S.C. 154(b) by 0 days.

(21) Appl. No.: 15/732,480

(22) Filed: Nov. 16, 2017

(65) Prior Publication Data

US 2018/0084689 P1 Mar. 22, 2018

(51) Int. Cl.
*A01H 5/02* (2018.01)

(52) U.S. Cl.
USPC ..... Plt./255
CPC ..... *A01H 5/02* (2013.01)

(58) Field of Classification Search
USPC ..... Plt./255
See application file for complete search history.

*Primary Examiner* — Annette H Para
(74) *Attorney, Agent, or Firm* — James R. Holm

(57) ABSTRACT

A new and distinct *gardenia* plant named '4KIMYMJ01' particularly distinguished by flowers that are double-flowered with early flowering and increased flower production, dense compact branching habit with compact, dark green leaves, uniform, compact and mounding growth habit under standard production practices and increased tolerance to root diseases, is disclosed.

5 Drawing Sheets

Figure 1:
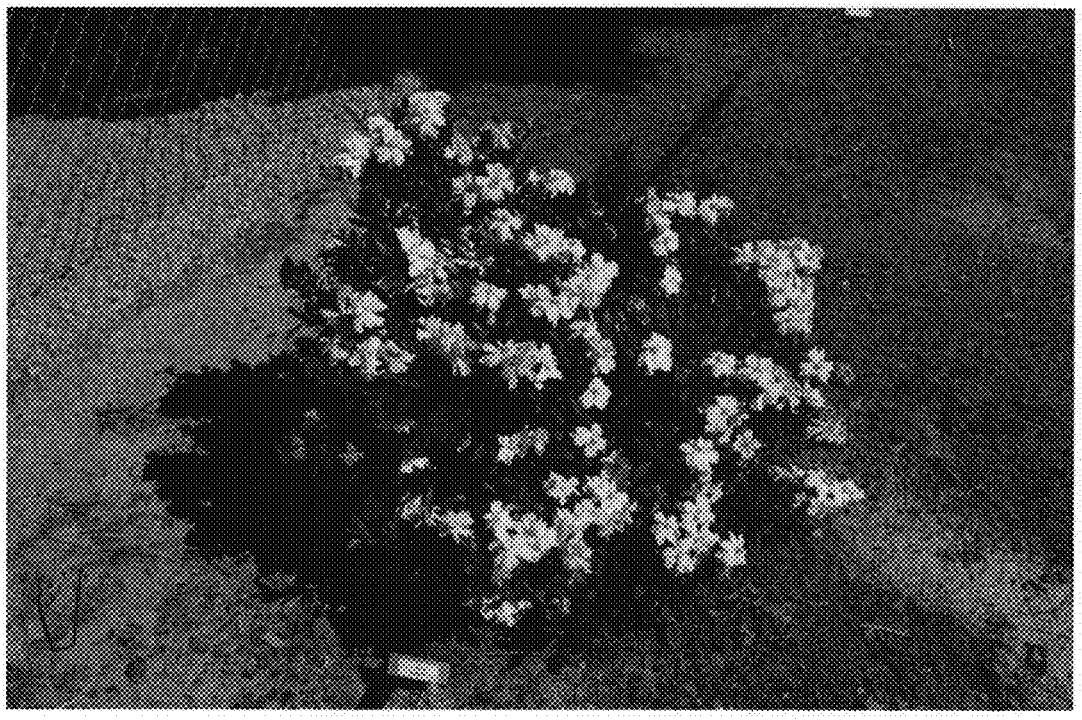

Genus and species: *Gardenia jasminoides.*
Variety denomination:
'4KIMYMJ01'.

BACKGROUND OF THE NEW PLANT

The present invention comprises a new and distinct variety of *gardenia* plant, botanically known as *Gardenia jasminoides*, and hereinafter referred to by the variety name '4KIMYMJ01'. This new *gardenia* plant originated from an open pollination conducted in 2009 in Dearing, Ga. between the female *gardenia* plant 'Frostproof' (unpatented) and an unknown male *gardenia* plant. The objective of the breeding program was to create a new *gardenia* plant with an early blooming habit, double-flowered, compact growth habit, easy-to-grow, and plants exhibiting cold hardiness.

Approximately 1400 progeny seeds resulting from said open pollination were planted in 2009. In 2010, progeny seedlings were planted in 2.25 inch liner cups and then in 2011 progeny seedlings were planted in 1-gallon containers. In 2013, progeny seedlings were planted in 3-gallon containers, inoculated with *Phytophthora cinnamomi*, and grown to evaluate disease response and production characteristics. The new variety was selected by the inventor as a single plant within said progeny in a controlled environment in Dearing, Ga. The new variety was selected based on its response to drought stress, disease, cold hardiness, and unique flowering and growth characteristics. '4KIMYMJ01' was first reproduced asexually by vegetative semi-softwood stem cuttings in October 2013 in Dearing, Ga. '4KIMYMJ01' has been found to retain its distinctive characteristics and has been found to be stable and reproduce true-to-type through two successive generations of asexual reproduction by vegetative semi-softwood stem cuttings.

Plant Breeder's Rights for this variety have not been applied for. '4KIMYMJ01' has not been made publicly available or sold anywhere in the world prior to the effective filing date of this application.

SUMMARY OF THE INVENTION

The new *gardenia* variety has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new *gardenia* variety when grown under normal horticultural practices in Dearing, Ga. The combination of these characteristics distinguishes '4KIMYMJ01' as a new and distinct variety of *gardenia:*

1. Flowers that are double-flowered with early flowering and increased flower production;
2. Dense branching habit with compact, dark green leaves;
3. Uniform, compact and mounding growth habit under standard production practices; and
4. Increased tolerance to root diseases.

DESCRIPTION OF THE PHOTOGRAPHS

This new *gardenia* is illustrated by the accompanying photographs which show the overall plant habit including flowers and foliage of the plant. The colors shown are as true as can be reasonably obtained by conventional photographic procedures. The photographs are of 3.6, 4 and 8-year-old plants grown in the ground and in 3-gallon containers in Dearing, Ga. The photographs were taken in May 2017 in Dearing Ga. under natural light and natural shade. Colors in the photographs may differ slightly from the color values cited in the botanical description which accurately describes the colors of the new variety.

FIG. 1. shows the original seedling and its overall habit, including flowers and foliage.

Figure 2:
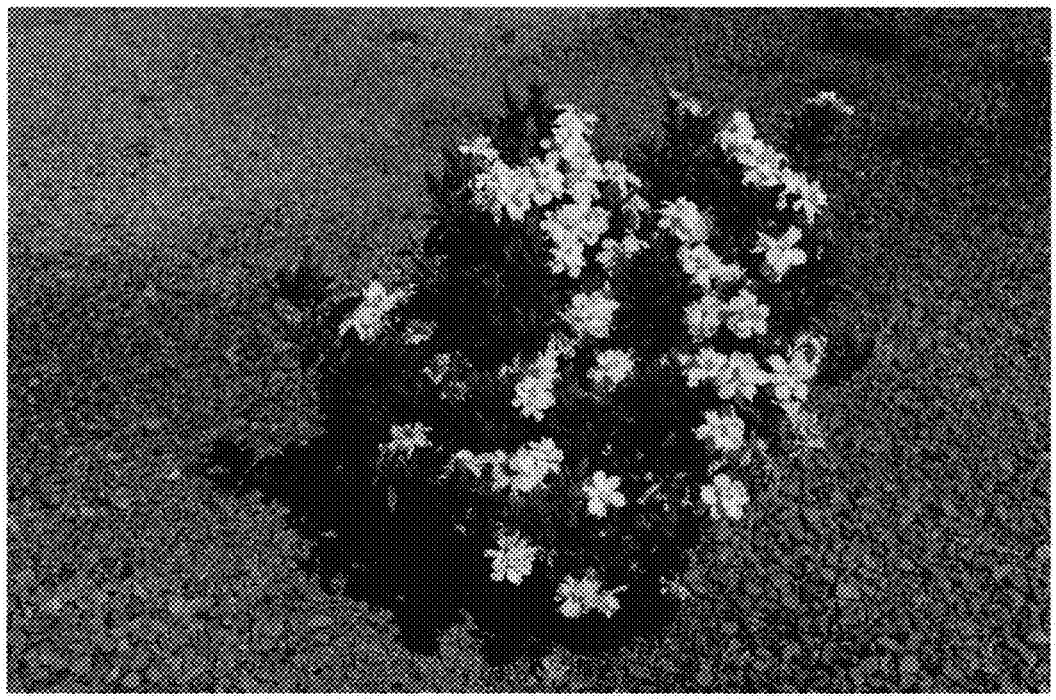

FIG. 2. shows a 3.6-year-old container grown plant.

Figure 3:
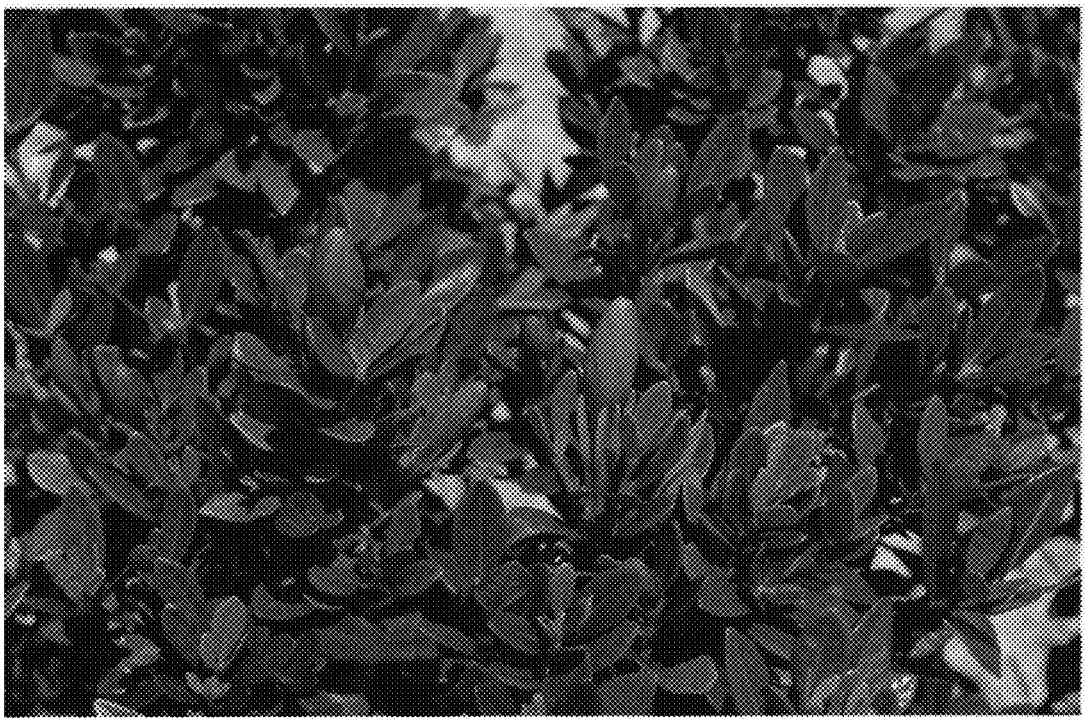

FIG. 3. shows typical foliage and flower buds.

Figure 4:
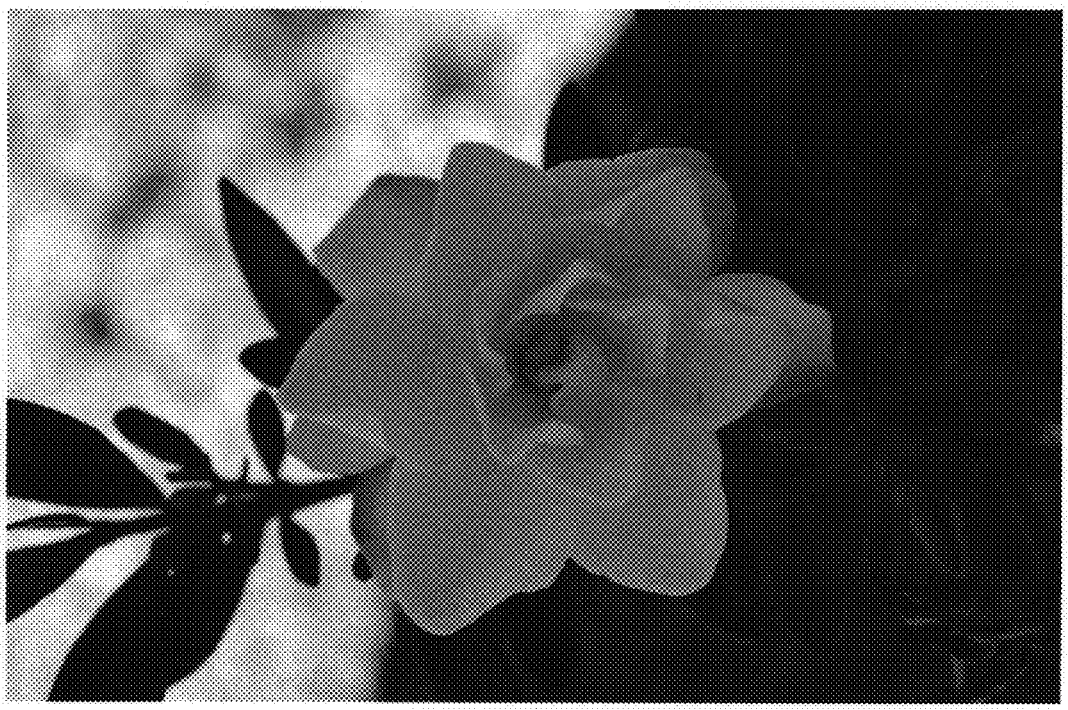

FIG. 4. shows a view of a typical mature flower.

Figure 5:
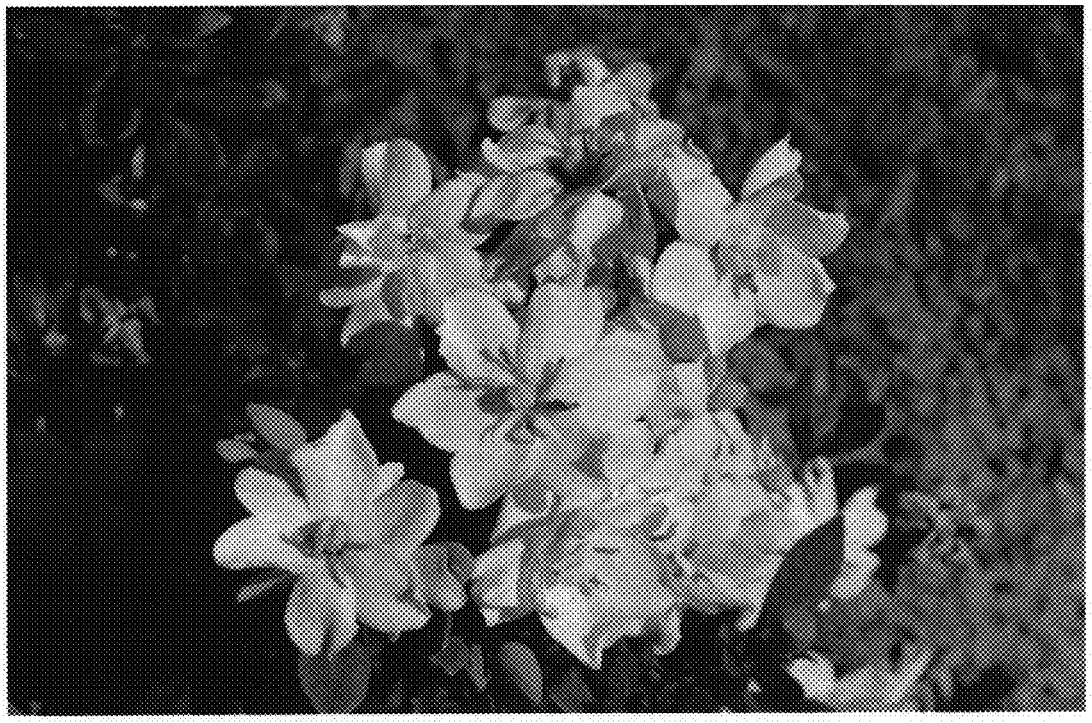

FIG. 5. shows flower forms with various reproductive structures present.

DESCRIPTION OF THE NEW VARIETY

In the following description, color references are made to The Royal Horticultural Society Colour Chart, Sixth Edition, except where general terms of ordinary dictionary significance are used.

The following observations and measurements describe plants grown in the ground and in 3-gallon containers when grown outdoors under a natural photoperiod in full sun in Dearing, Ga. Detailed descriptions were taken in 2016 and 2017 from approximately 3-year-old plants grown from single vegetative semi-softwood stem cuttings. Measurements and numerical values represent averages of typical plant types.

DETAILED BOTANICAL DESCRIPTION

Classification:

*Family.*—Rubiaceae.

*Botanical.—Gardenia jasminoides.*

*Common.—Gardenia.*

*Denomination.*—'4KIMYMJ01'.

Parentage:

*Female or seed parent.—Gardenia jasminoides* plant 'Frostproof' (unpatented).

*Male or pollen parent.*—Unknown.

Propagation:

*Type.*—Vegetative semi-softwood stem cuttings.

*Time to initiate roots.*—14 to 21 days.

*Time to produce a rooted young plant.*—5 to 6 months, a cutting placed in rooting media in approximately September to October will be rooted and ready to pot in approximately February to March the following year, rooting time is shorter during warmer months.

Root description: Fibrous.

Plant description:

*Plant type.*—Evergreen shrub.

*Growth habit.*—Compact, mounding.

*Height.*—58.0 cm after 4 years of growth and 78.0 cm after 8 years of growth.

*Plant spread.*—62.0 cm after 4 years of growth and 87.0 cm after 8 years of growth.

*Growth rate.*—11.0 cm to 18.0 cm per year depending on environmental conditions and plant's age, growth rate slows as plants mature.

*Plant vigor.*—Vigorous when young, vigor slows as plants mature.

*Branching habit.*—Freely branching.

*Primary branches* (*one year or older*).—Length: 18.0 cm per year. Diameter: 0.5 cm at one year of age. Strength: Pliable during the first year's growth and becoming stiff the second year. Color: Mature branches: Grey-brown, N199B and 199D. Young branches: Brown, 200D with areas of yellow-green, 144A. Texture: Exfoliating, no pubescence.

*Lateral branches* (*less than one year old*).—Length: 5.3 cm per flush. Diameter: 0.2 cm. Strength: Flexible. Aspect: 10 to 45 degree angles. Texture: Setulose pubescence. Color: Immature branches are yellow-green, 144B, and aging to yellow-green, 144A, and funny maturing to yellow-green, N148A. Internode length: 1.68 cm.

Foliage description:

*Leaf type.*—Simple.

*Leaf arrangement.*—Primarily opposite with some whorled leaves, 2 to 3 per node.

*Average mature leaf size.*—Length: 3.48 cm. Width: 1.14 cm.

*Mature leaf shape.*—Oblanceolate.

*Leaf apex.*—Acute to acuminate.

*Leaf base.*—Attenuate to crunate.

*Leaf attachment.*—Petiolate with persistent sheathing stipules at the apex of the node.

*Leaf margin.*—Entire.

*Internode length.*—1.72 cm.

*Leaf texture.*—Upper surface: Glabrous, waxy. Bottom surface: Glabrous.

*Leaf color.*—Young leaves: Upper surface: Yellow-green, 146A. Lower surface: Green, 139D. Mature leaves: Upper surface: Green, 139A. Lower surface: Green, 138B.

*Leaf venation.*—Type: Pinnate. Color: Upper surface: Yellow-green, 144A. Lower surface: Yellow-green, 144C.

Flower description:

*Bloom period.*—Primary bloom period is typically May through mid-May in Dearing, Ga., blooming occurs sporadically through summer and into fall.

*Type.*—Perfect flower, complete and near complete.

*Arrangement.*—Solitary flower at apex of stems and occasionally at leaf axils.

*Peduncle.*—Length: 0.5 cm. Diameter: 0.2 cm. Color: Yellow-green, 144A. Texture: Glabrous. Strength: Slightly pliable, breakable with force.

*Height* (*depth*).—5.0 cm from attachment to the stem.

*Diameter.*—6.0 cm by 6.5 cm.

*Facing direction.*—Outward.

*Persistence.*—Self-cleaning.

*Fragrance.*—Sweet fragrance typical of *gardenia* flowers.

*Flower tube.*—Length: 2.0 cm. Width at widest point: 1.0 cm. Width at narrowest point: 0.4 cm. Texture: Setulose pubescence on the outside surface.

*Petals.*—Arrangement: 2 rows of petals with 1 row of petaloids. Length: Outer row: 2.5 cm. Second row: 2.3 cm. Third row: Petaloids measuring up to 2.1 cm in length from point of fusion with the flower tube with smaller, irregular petaloids present. Width: Outer row: 1.5 cm. Second row: 1.6 cm. Third row: Petaloids measuring up to 1.6 cm with smaller, irregular petaloids present. Apex: Unevenly rounded. Base: Fused tube. Shape: Obovate. Margin: Entire, undulating with some overlap. Quantity: 5 to 6 per row. Texture: Glabrous. Color: Outer surface at maturity: White, NN155D, with a strip on the outer petals of yellow-green, 150B. Inner surface at maturity: White, NN155D and 155C, and yellow-green, 145B. Upper surface at fading: Yellow, 10D. Lower surface at fading: Close to white, 155C.

*Buds.*—Shape: Oblong. Length: 4.1 cm. Diameter: 1.25 cm. Color: Green, 143C. Texture: Glaborous on the swollen area of the petals, lanulose and setulose pubescence on the tube area of the bud.

*Calyx/sepals.*—Quantity of sepals per flower: 5 to 6. Calyx arrangement: Star-shaped. Sepal shape: Lanceolate and fused to the base. Length: Calyx is 1.0 cm with sepals extending 1.5 cm beyond calyx. Width: 0.8 cm at the base of the flower tube. Apex: Acute. Base: Fused. Margin: Entire. Texture: Smooth. Color (both inner and outer surfaces): Yellow-green at the apex, 144C, and yellow-green at the base, 144A.

Reproductive organs:

*Stamens.*—Quantity: Varying in presence, 0 to 6 with 5 to 6 petaloid stamens most commonly present. Length: 2.1 cm. Width: 1.6 cm. Anthers: Aspect: Curving and fused with the petaloids. Length: Approximately 1.0 cm. Width: 0.2 cm. Color: Grey-brown, N199D. Pollen: Amount: Moderate. Color: Yellow, 6D.

*Pistils.*—Quantity: 1 per flower. Length: 4.0 cm. Style: Length: 2.8 cm. Color: White, NN155A. Stigma: Shape: Obovate with 3 to 4 irregular shaped lobes, stigma measure 0.7 cm in length by 0.5 cm in width. Color: Yellow, 5C. Ovary: Type: Inferior within calyx cup. Length: 0.5 cm. Diameter: 0.7 cm.

Cold tolerance: Hardy to USDA zone 7 with current evaluations of cold hardiness in USDA zone 6.

Disease and pest tolerance: Tolerance to root diseases has been observed, but not under controlled conditions. Susceptible to insect pests common to *gardenia*, such as scale and whitefly.

Fruit and seed set: None observed.

Drought tolerance: Tolerance to periodic drought stress has been observed in container grown plants.

COMPARISON WITH PARENTAL VARIETIES

'4KIMYMJ01' differs from the female parent plant 'Frostproof' (unpatented) in that '4KIMYMJ01' has a denser and more compact branching habit than 'Frostproof'. Additionally, '4KIMYMJ01' has more rounded and darker green foliage than 'Frostproof'.

COMPARISON WITH KNOWN CULTIVARS

'4KIMYMJ01' differs from the commercial *gardenia* variety 'Double Mint' (U.S. Plant Pat. No. 23,507) in that '4KIMYMJ01' has a more compact growth habit with plants measuring 58.0 cm by 62.0 cm after 4 years of growth, whereas plants of 'Double Mint' measure 68.0 cm by 70.0 cm after 4 years of growth. Additionally, when compared to 'Double Mint', '4KIMYMJ01' has denser internode spacing of 1.68 cm, whereas 'Double mint' has an internode spacing of 2.3 cm. Furthermore '4KIMYMJ01' an improved production consistency under a production setting in Dearing, Ga.

When compared to the commercial *gardenia* variety 'Radicans' (unpatented), '4KIMYMJ01' has a more upright, mounded growth habit and more rounded foliage, whereas 'Radicans' has a more low spreading growth habit. Additionally, when compared to 'Radicans', '4KIMYMJ01' has an improved production consistency under a production setting in Dearing, Ga.

When compared to the commercial *gardenia* variety 'August Beauty' (unpatented) '4KIMYMJ01' blooms on average 2 weeks earlier than 'August Beauty'.

I claim:

1. A new and distinct variety of *gardenia* plant named '4KIMYMJ01', substantially as illustrated and described herein.

* * * * *